US012616618B2

(12) United States Patent
Takamatsu et al.

(10) Patent No.: US 12,616,618 B2
(45) Date of Patent: May 5, 2026

(54) ABSORBER WITH PARTICLES HAVING WATER ABSORPTION AND WETTABILITY PROPERTIES

(71) Applicant: SUMITOMO SEIKA CHEMICALS CO., LTD., Kako (JP)

(72) Inventors: Kazuyoshi Takamatsu, Himeji (JP); Chiho Onita, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 511 days.

(21) Appl. No.: 18/005,309

(22) PCT Filed: Jun. 30, 2021

(86) PCT No.: PCT/JP2021/024766
§ 371 (c)(1),
(2) Date: Jan. 12, 2023

(87) PCT Pub. No.: WO2022/014335
PCT Pub. Date: Jan. 20, 2022

(65) Prior Publication Data
US 2023/0263673 A1 Aug. 24, 2023

(30) Foreign Application Priority Data
Jul. 17, 2020 (JP) ................................. 2020-122770

(51) Int. Cl.
*A61F 13/53* (2006.01)
(52) U.S. Cl.
CPC .. *A61F 13/53* (2013.01); *A61F 2013/530489* (2013.01)

(58) Field of Classification Search
CPC ......... A61F 13/53; A61F 2013/530489; A61L 15/18; A61L 15/24; B01J 13/14; B01J 20/26; B01J 20/261; B01J 20/262; B01J 20/267; B01J 20/28004; B01J 20/28011;
(Continued)

(56) References Cited

U.S. PATENT DOCUMENTS

2017/0014801 A1 1/2017 Ikeuchi et al.
2021/0298965 A1* 9/2021 Noda ..................... B01J 20/267

FOREIGN PATENT DOCUMENTS

CN 103347548 10/2013
CN 103502287 1/2014
CN 109071830 12/2018
(Continued)

OTHER PUBLICATIONS

International Search Report of PCT/JP2021/024766, Sep. 7, 2021, 2 pages.
(Continued)

*Primary Examiner* — Michele Kidwell
(74) *Attorney, Agent, or Firm* — HSML P.C.

(57) ABSTRACT

One aspect of the present invention relates to an absorber containing water-absorbing resin particles, in which the water-absorbing resin particles include water-absorbing resin particles (A) which have a water absorption rate of 55 to 150 seconds according to a Vortex method and have a non-pressure DW 5-minute value of 36 mL/g or less, and the content of the water-absorbing resin particles (A) based on a total amount of the water-absorbing resin particles is 9 to 90 mass %.

13 Claims, 2 Drawing Sheets

(58) Field of Classification Search
CPC . B01J 20/28016; B01J 20/321; B01J 20/3293
See application file for complete search history.

(56) References Cited

FOREIGN PATENT DOCUMENTS

| | | | | | | |
|----|----------|---|---------|---|------|----------|
| EP | 3896117 | | 10/2021 | | | |
| JP | H6-345819 | | 12/1994 | | | |
| JP | H9-510889 | | 11/1997 | | | |
| JP | 2004-517173 | | 6/2004 | | | |
| JP | 2014-505151 | | 2/2014 | | | |
| JP | 2016-196659 | | 11/2016 | | | |
| JP | 2018-021090 | | 2/2018 | | | |
| JP | 2018-021133 | | 2/2018 | | | |
| JP | 2018-127508 | * | 8/2018 | ............... | C08J 3/12 |
| JP | 2020-037625 | | 3/2020 | | | |
| JP | 2020-125472 | | 8/2020 | | | |
| WO | 95/026209 | | 10/1995 | | | |
| WO | 02/053199 | | 7/2002 | | | |
| WO | 2011/086844 | | 7/2011 | | | |
| WO | 2012/107432 | | 8/2012 | | | |
| WO | 2014/017100 | * | 1/2014 | ............ | A61F 13/53 |
| WO | 2015/129917 | | 9/2015 | | | |
| WO | 2017/200085 | | 11/2017 | | | |
| WO | 2018/147317 | | 8/2018 | | | |
| WO | 2018/225815 | | 12/2018 | | | |
| WO | 2020122208 | | 6/2020 | | | |
| WO | 2020122209 | | 6/2020 | | | |

OTHER PUBLICATIONS

International Preliminary Report on Patentability of PCT/JP2021/024766, Jan. 26, 2023, 6 pages.
The extended European Search Report issued in EP Patent Application No. 21842434.9, dated Jul. 5, 2024, 9 pages.

* cited by examiner

ABSORBER WITH PARTICLES HAVING WATER ABSORPTION AND WETTABILITY PROPERTIES

TECHNICAL FIELD

The present invention relates to an absorber.

BACKGROUND ART

In the related art, as absorbing articles for absorbing a liquid containing water such as urine as a main component, absorbers containing water-absorbing resin particles are used. For example, Patent Literature 1 discloses a method of producing water-absorbing resin particles having a particle size suitable for use in absorbing articles such as diapers, and Patent Literature 2 discloses a method of using a hydrogel-forming absorbing polymer having specific saline flow inductivity, performance under pressure and the like as an absorbing member effective for accommodating an aqueous component solution.

CITATION LIST

Patent Literature

[Patent Literature 1] JP H06-345819 A
[Patent Literature 2] JP H09-510889 A

SUMMARY OF INVENTION

Technical Problem

Regarding the performance required for an absorbing article, it is important that a liquid not easily leak even when the article is worn for a long time. As a method of minimizing liquid leakage, it is conceivable to use water-absorbing resin particles having a high water absorption rate (a large water retention capacity after water absorption) as a material constituting an absorber. However, water-absorbing resin particles having a high water absorption rate have poor liquid diffusibility, and as a result, liquid leakage from the absorbing article cannot be sufficiently minimized. Specifically, when water-absorbing resin particles swell with a liquid, gaps inherently present between water-absorbing resin particles are filled with swollen gel-like water-absorbing resin particles, which makes it difficult for the liquid to pass through the gaps. Such a phenomenon is generally referred to as a gel-blocking phenomenon. As a result, the diffusibility of the liquid in the absorber becomes low, the entire amount of water-absorbing resin particles contained in the absorber cannot be effectively used, and the liquid that has not been absorbed by the water-absorbing resin particles tends to leak from the absorber.

In order to inhibit the gel-blocking phenomenon, when water-absorbing resin particles having a low water absorption rate (a small water retention capacity after water absorption) are used as a material constituting the absorber, the gel-blocking phenomenon hardly occurs, and the liquid easily diffuses in the absorber. However, when water-absorbing resin particles having a low water absorption rate are used, a rate (absorption rate) at which the absorber absorbs the liquid tends to be excessively low. In addition, in the water-absorbing resin particles having a low water absorption rate, re-wet (leakage of liquid that has been temporarily absorbed by the water-absorbing resin particles) tends to occur due to pressurization.

An objective of the present invention is to provide an absorber having an excellent liquid diffusibility, a small re-wet amount, and a high absorption rate.

Solution to Problem

One aspect of the present invention is an absorber containing water-absorbing resin particles, in which the water-absorbing resin particles include water-absorbing resin particles (A) which have a water absorption rate of 55 to 150 seconds according to a Vortex method and have a non-pressure DW 5-minute value of 36 mL/g or less, and the content of the water-absorbing resin particles (A) based on a total amount of the water-absorbing resin particles is 9 to 90 mass %.

Advantageous Effects of Invention

According to the present invention, it is possible to provide an absorber having an excellent liquid diffusibility, a small re-wet amount, and a high absorption rate.

DESCRIPTION OF EMBODIMENTS

Figure 1:
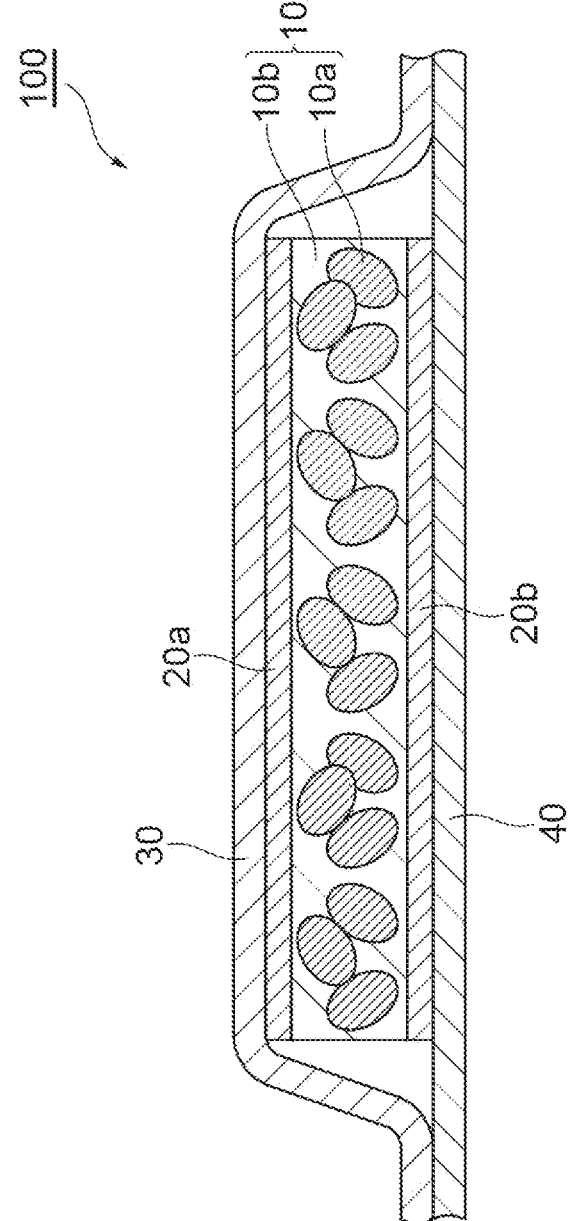
FIG. 1 is a cross-sectional view showing an example of an absorbing article.

Hereinafter, several embodiments of the present invention will be described in detail. However, the present invention is not limited to the following embodiments.

In this specification, "acryl" and "methacryl" are collectively referred to as "(meth)acryl." Similarly, "acrylate" and "methacrylate" are denoted as "(meth)acrylate." "(Poly)" means both with and without the "poly" prefix. In the numerical ranges stated stepwise in this specification, the upper limit value or the lower limit value of the numerical range of a certain stage can be arbitrarily combined with the upper limit value or the lower limit value of the numerical range in another stage. In the numerical ranges stated in this specification, the upper limit value or the lower limit value of the numerical range may be replaced with values shown in examples. Materials exemplified in this specification may be used alone or two or more thereof may be used in combination. Unless otherwise specified, when there are a plurality of substances corresponding to components in the composition, the content of each component in the composition means a total amount of the plurality of substances present in the composition. "Room temperature" refers to 25±2° C. The term "layer" includes not only a shape structure formed over the entire surface but also a shape structure formed partially when observed in a plan view. "Physiological saline solution" refers to a 0.9 mass % aqueous sodium chloride solution.

[Absorber]

An absorber according to the present embodiment includes water-absorbing resin particles that include water-absorbing resin particles (A) which have a water absorption rate of 55 to 150 seconds according to a Vortex method and a non-pressure DW 5-minute value of 36 mL/g or less. The content of the water-absorbing resin particles (A) in the absorber based on a total amount of the water-absorbing resin particles is 9 to 90 mass %.

When the water absorption rate of the water-absorbing resin particles (A) is 55 seconds or more, the occurrence of the gel-blocking phenomenon can be easily minimized. When the water absorption rate of the water-absorbing resin particles (A) is 150 seconds or less, water absorption is excellent and a dry feeling tends to be improved. The water absorption rate of the water-absorbing resin particles (A) may be 58 seconds or more, 60 seconds or more, or 61 seconds or more, and is preferably 63 seconds or more, 65 seconds or more, or 67 seconds or more so that the effects of the present invention are more likely to be exhibited. In addition, the water absorption rate may be 130 seconds or less, 110 seconds or less, or 90 seconds or less, and is preferably 80 seconds or less, 75 seconds or less, or 70 seconds or less. The water absorption rate according to a Vortex method is measured according to Japanese Industrial Standards JIS K 7224 (1996) as described in examples to be described below.

When the non-pressure DW 5-minute value of the water-absorbing resin particles (A) is 36 mL/g or less, the amount of water absorbed in the initial stage of water absorption is curbed, and therefore the diffusibility of urine increases, which results in improvement of the absorption rate and improvement in absorber utilization (utilization of the entire water-absorbing resin particles contained in the absorber). In order to achieve both an excellent liquid diffusibility and excellent re-wet amount, the non-pressure DW 5-minute value of the water-absorbing resin particles (A) may be 35 mL/g or less, 34 mL/g or less, or 33 mL/g or less, and is preferably 30 mL/g or less, 20 mL/g or less, or 15 mL/g or less, and more preferably 10 mL/g or less, 8 mL/g or less, or 5 mL/g or less. The lower limit value of the non-pressure DW 5-minute value may be 1 mL/g or more. The non-pressure DW 5-minute value is measured by a method described in examples to be described below. The non-pressure DW 5-minute value is a water absorption rate represented by the amount of the physiological saline solution absorbed by the water-absorbing resin particles within 5 minutes after contact with the physiological saline solution under no pressure. The non-pressure DW is represented by the absorbed amount [mL] per 1 g of water-absorbing resin particles before the physiological saline solution is absorbed.

In order to achieve both an excellent liquid diffusibility and an excellent re-wet amount more easily, the water retention capacity of the physiological saline solution containing the water-absorbing resin particles (A) may be, for example, 16 g/g or more, 18 g/g or more, or 20 g/g or more. The water retention capacity of the physiological saline solution may be 50 g/g or less, 45 g/g or less, or 40 g/g or less, and is preferably 35 g/g or less or 30 g/g or less, and more preferably 25 g/g or less or 22 g/g or less. The water retention capacity of the physiological saline solution is measured by a method described in examples to be described below.

When the absorber according to the present embodiment contains 9 to 90 mass % of the water absorbing resin particles (A) based on a total amount of the water-absorbing resin particles, it can exhibit an excellent liquid diffusibility, a small re-wet amount, and a high absorption rate. In consideration of an excellent re-wet amount and a high absorption rate, the content of the water-absorbing resin particles (A) may be 10 mass % or more, 12 mass % or more, or 16 mass % or more, and is preferably 20 mass % or more, 30 mass % or more, or 33 mass % or more, and more preferably 50 mass % or more, 55 mass % or more, 60 mass % or more, or 66 mass % or more. In order to achieve both an excellent liquid diffusibility and a high absorption rate, the content of the water-absorbing resin particles (A) may be 88 mass % or less, 86 mass % or less, 85 mass % or less, or 84 mass % or less.

The configuration of the water-absorbing resin particles (A) is not particularly limited as long as it is a resin that satisfies having the above water absorption rate and non-pressure DW 5-minute value. The water-absorbing resin particles (A) may be, for example, coated resin particles having a water-insoluble coating layer that covers at least a part of the surface of the water-absorbing resin particles.

The water-absorbing resin particles constituting the coated resin particles are not particularly limited as long as they are composed of a water-absorbing resin, and for example, may contain a crosslinked polymer formed by polymerization of monomers containing ethylenically unsaturated monomers. The crosslinked polymer can have monomer units derived from ethylenically unsaturated monomers. The water-absorbing resin particles can be produced, for example, by a method including a process of polymerizing monomers including ethylenically unsaturated monomers. Examples of polymerization methods include a reverse phase suspension polymerization method, an aqueous solution polymerization method, a bulk polymerization method, and a precipitation polymerization method.

The ethylenically unsaturated monomers may be water-soluble ethylenically unsaturated monomers (ethylenically unsaturated monomers having a solubility of 1 g or more at 98° C. in 100 g of water). Examples of water-soluble ethylenically unsaturated monomers include (meth)acrylic acid and its salts, 2-(meth)acrylamido-2-methylpropane-sulfonic acid and its salts, (meth)acrylamide, N,N-dimethyl (meth)acrylamide, 2-hydroxyethyl (meth)acrylate, N-methylol(meth)acrylamide, polyethylene glycol mono(meth)acrylate, N,N-diethylaminoethyl (meth)acrylate, N,N-diethylaminopropyl (meth)acrylate, and diethylaminopropyl (meth)acrylamide. When the ethylenically unsaturated monomer has an amino group, the amino group may be quaternized. The ethylenically unsaturated monomers may be used alone or two or more thereof may be used in combination.

When the ethylenically unsaturated monomer has an acid group, the acid group may be neutralized with an alkaline neutralizing agent and then used in a polymerization reaction. The neutralization degree of the ethylenically unsaturated monomer with respect to an alkaline neutralizing agent may be, for example, 10 to 100 mol %, 50 to 90 mol %, or 60 to 80 mol % of acidic groups in the ethylenically unsaturated monomer.

In consideration of ease of industrial availability, the ethylenically unsaturated monomers may include at least one compound selected from the group consisting of (meth)acrylic acid and its salts, acrylamide, methacrylamide, and N,N-dimethylacrylamide. The ethylenically unsaturated monomers may include at least one compound selected from the group consisting of (meth)acrylic acid and its salts, and acrylamide.

As monomers for obtaining water-absorbing resin particles, monomers other than the above ethylenically unsaturated monomers may be used. For example, such monomers can be used by being mixed with an aqueous solution containing the above ethylenically unsaturated monomers. The amount of ethylenically unsaturated monomers used with respect to a total amount of monomers may be 70 to 100 mol %. The proportion of (meth)acrylic acid and its salts with respect to a total amount of monomers may be 70 to 100 mol %.

Crosslinking may occur according to self-crosslinking during polymerization, but crosslinking may be promoted using an internal crosslinking agent. When the internal crosslinking agent is used, it is easy to control water absorption properties (water retention capacity, etc.) of the water-absorbing resin particles. The internal crosslinking agent is generally added to a reaction solution during the polymerization reaction.

The water-absorbing resin particles may be crosslinked (surface crosslink) in the vicinity of surfaces. In addition, the water-absorbing resin particles may be composed of only polymer particles (crosslinked polymer), and may further include, for example, various additional components selected from among gel stabilizers, metal chelating agents, and fluidity improving agents (lubricants). The additional components can be disposed inside polymer particles, on the surfaces of polymer particles or both thereof. The additional component may be a fluidity improving agent (lubricant). The fluidity improving agent may contain inorganic particles. Examples of inorganic particles include silica particles such as amorphous silica.

The shape of the water-absorbing resin particles is not particularly limited, and may be, for example, a substantially spherical shape, a crushed shape or a granular shape, and may be a shape in which primary particles having these shapes are aggregated.

The median particle size of the water-absorbing resin particles may be 100 to 800 μm, 150 to 700 μm, 200 to 600 μm, or 250 to 500 μm. The median particle size can be measured by the following method.

<Method of Measuring Median Particle Size>

Regarding JIS standard sieves, from the top, a sieve having an opening of 600 μm, a sieve having an opening of 500 μm, a sieve having an opening of 425 μm, a sieve having an opening of 300 μm, a sieve having an opening of 250 μm, a sieve having an opening of 180 μm, a sieve having an opening of 150 μm, and a receiver are combined in that order, 50 g of water-absorbing resin particles are put into the uppermost combined sieve, and classified using a low tap shaker (manufactured by IIDA-Seisakusho Japan Corporation) according to JIS Z 8815 (1994). After classification, the mass of particles remaining on each sieve is calculated as a mass percentage with respect to the total amount to obtain a particle size distribution. Regarding the particle size distribution, by accumulating particles in descending order of particle sizes on the sieves, the relationship between the sieve opening and the cumulative value of the mass percentage of the particles remaining on the sieve is plotted on logarithmic probability paper. When plots on the probability paper are connected with a straight line, the particle size corresponding to a cumulative mass percentage of 50 mass % is obtained as a median particle size.

The water-insoluble coating layer constituting the coated resin particles is a layer containing a water-insoluble component. In this specification, the water-insoluble component may include not only a substance that is completely insoluble in water but also a substance that is slightly soluble in water (a poorly water-soluble substance). The solubility of the water-insoluble component in 100 g of water is, for example, less than 10 g at 98° C., preferably less than 5 g, more preferably less than 3 g, and still more preferably less than 1 g.

The coating layer may be a layer containing at least one water-insoluble component selected from among water-insoluble organic compounds and water-insoluble inorganic compounds.

Examples of water-insoluble organic compounds include polyurethanes, polyolefins, polyesters, polyamides, polystyrenes, polycarbonates, polyacrylates, polyacetals, and acid-modified products thereof. The water-insoluble organic compound preferably contains at least one selected from the group consisting of polyolefins, polyurethanes, polyesters, and acid-modified products thereof, more preferably contains at least one selected from the group consisting of polyolefins, polyurethanes, and acid-modified products thereof, and still more preferably contains acid-modified polyolefins and/or polyurethanes. These organic compounds may be used alone or a plurality thereof may be used in combination.

When the water-insoluble component is acid-modified, the water-insoluble component may be modified with at least one acid anhydride selected from the group consisting of maleic anhydride, succinic anhydride, and phthalic anhydride. The object to be modified with an acid anhydride is preferably a polyolefin, more preferably at least one selected from the group consisting of polyethylene, polypropylene, and ethylene/propylene copolymers, and still more preferably an ethylene/propylene copolymer. In addition, the acid anhydride used for medication is preferably maleic anhydride.

The polyurethane is a reaction product of a polyol and a polyisocyanate. Examples of polyols include polyether polyol, polyester polyol, polybutadiene polyol, and hydrogenated polybutadiene polyol. Examples of polyisocyanates include aromatic isocyanates such as diphenylmethane diisocyanate, dimethyldiphenylmethane diisocyanate, tolylene diisocyanate, xylylene diisocyanate, and p-phenylene diisocyanate; alicyclic isocyanates such as dicyclohexylmethane diisocyanate, and isophorone diisocyanate; and aliphatic isocyanates such as hexamethylene diisocyanate.

Examples of water-insoluble inorganic compounds include light anhydrous silicic acid, calcium silicate, silicon dioxide (silica), talc, silicon monoxide, and synthetic hydrotalcite. These inorganic compounds may be used alone or a plurality of types thereof may be used in combination. When a coating layer is formed, at least one of silicon dioxide and talc is preferably used, and silicon dioxide is more preferably used because it can exhibit relatively high water permeability. Silicon dioxide may be hydrophilic or hydrophobic, but hydrophobic silicon dioxide is preferable because the above water absorption rate and non-pressure DW 5-minute value of the water-absorbing resin particles can be easily achieved.

When a coating layer is formed on water-absorbing resin particles, the water-absorbing resin particles and a coating material may be mixed, and the coating layer may be formed on at least a part of the surface of the water-absorbing resin particles. The coating material is, for example, a component that can form the above coating layer or a material forming the component. For example, when the coating layer contains a polyurethane, the coating material may contain a polyurethane itself or may contain a polyol and a polyisocyanate which are materials forming the polyurethane.

The method of forming a coating layer is not particularly limited. For example, a coating layer can be formed by dispersing water-absorbing resin particles and then bringing a coating material into contact with the dispersed water-absorbing resin particles. Specifically, when a coating material is dissolved in a dispersion medium in which polymer particles are dispersed, water-absorbing resin particles and a coating material are added to the dispersion medium, and a coating layer may be formed on the surface of the water-absorbing resin particles. In addition, when a polyol and a polyisocyanate are used as the coating material, a polyol aqueous solution is mixed with a dispersion liquid of water-absorbing resin particles to bringing the polyol into contact with the water-absorbing resin particles, the solution containing a polyisocyanate is then mixed to polymerize the polyol and the polyisocyanate, and thereby a coating layer containing a polyurethane may be formed on the surface of polymer particles.

The dispersion medium may contain a hydrocarbon solvent. Examples of hydrocarbon solvents include chain aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methyl cyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene.

When a solid inorganic compound is used as a coating material, a coating layer can be formed by compressing the coating material on the surface of the water-absorbing resin particles using a particle compounding device. Specifically, predetermined amounts of water-absorbing resin particles and a solid inorganic compound are put into the particle compounding device. Then, by rotating stirring blades of the device, stress (compressive stress and shear stress) is applied to the water-absorbing resin particles and the inorganic compound, the inorganic compound is compressed on the surface of the water-absorbing resin particles due to the stress, and thereby coated resin particles are produced.

The absorber according to the present embodiment contains water-absorbing resin particles (B) different from the water-absorbing resin particles (A). The water-absorbing resin particles (B) have a water absorption rate according to a Vortex method or a non-pressure DW 5-minute value different from the water-absorbing resin particles (A). As the water-absorbing resin particles (B), water-absorbing resin particles in the related art may be used, for example, water-absorbing resin particles before the coating layer is formed with the above coated resin particles may be used.

In a condition in which at least one value of the water absorption rate according to a Vortex method and the non-pressure DW 5-minute value differs from that of the water-absorbing resin particles (A), the water absorption capacity of the water-absorbing resin particles (B) is not particularly limited. The water-absorbing resin particles (B) satisfy at least one of a water absorption rate of less than 55 seconds according to a Vortex method, a water absorption rate of more than 150 seconds according to a Vortex method, and a non-pressure DW 5-minute value of more than 36 mL/g.

The water absorption rate of the water-absorbing resin particles (B) according to a Vortex method may be, for example, 20 seconds or more or 25 seconds or more, and may be 160 seconds or less, 155 seconds or less, or 153 seconds or less, and may be 60 seconds or less, 55 seconds or less, or 53 seconds or less. The non-pressure DW 5-minute value of the water-absorbing resin particles (B) may be 5 mL/g or more or 9 mL/g or more, and is preferably 35 mL/g or more, 38 mL/g or more, 40 mL/g or more, or 45 mL/g or more, and more preferably 50 mL/g or more or 54 mL/g or more. The non-pressure DW 5-minute value of the water-absorbing resin particles (B) may be 65 mL/g or less or 60 mL/g, and is preferably 55 mL/g or less or 54 mL/g or less.

The water retention capacity of the physiological saline solution containing the water-absorbing resin particles (B)

may be 35 g/g or more, 38 g/g or more, or 40 g/g or more, and may be 60 g/g or less, 55 g/g or less, or 50 g/g or less.

The absorber according to the present embodiment may contain a fibrous material, and is, for example, a mixture containing water-absorbing resin particles and a fibrous material. The configuration of the absorber may be, for example, a configuration in which water-absorbing resin particles and a fibrous material are uniformly mixed, a configuration in which water-absorbing resin particles are interposed between fibrous materials formed in sheets or layers, or other configurations.

Examples of fibrous materials include finely pulverized wood pulp; cotton; cotton linters; rayon; cellulosic fibers such as cellulose acetate; synthetic fibers such as polyamides, polyesters, and polyolefins; and mixtures of these fibers. Fibrous materials may be used alone or two or more thereof may be used in combination. Hydrophilic fibers can be used as the fibrous material.

In order to improve shape retention before and during use of the absorber, fibers may be bonded together by adding an adhesive binder to the fibrous material. Examples of adhesive binders include heat-fusible synthetic fibers, hot-melt adhesives, and adhesive emulsions. Adhesive binders may be used alone or two or more thereof may be used in combination.

Examples of heat-fusible synthetic fibers include all-melting type binders such as polyethylene, polypropylene, and ethylene-propylene copolymers; and non-all-melting type binders composed of a side by side or core-sheath structure of a polypropylene and a polyethylene. In the above non-all-melting type binder, only the polyethylene part can be heat-fusible.

Examples of hot-melt adhesives include mixtures of base polymers such as an ethylene-vinyl acetate copolymer, a styrene-isoprene-styrene block copolymer, a styrene-butadiene-styrene block copolymer, a styrene-ethylene-butylene-styrene block copolymer, a styrene-ethylene-propylene-styrene block copolymer, and an amorphous polypropylene, and a tackifier, a plasticizer, an antioxidant and the like.

Examples of adhesive emulsions include polymers of at least one monomer selected from the group consisting of methyl methacrylate, styrene, acrylonitrile, 2-ethylhexyl acrylate, butyl acrylate, butadiene, ethylene, and vinyl acetate.

The absorber according to the present embodiment may contain inorganic powders (for example, amorphous silica), deodorants, antibacterial agents, pigments, dyes, fragrances, adhesives and the like. When water-absorbing resin particles include inorganic particles, the absorber may contain inorganic powders separately from inorganic particles in the water-absorbing resin particles.

The shape of the absorber according to the present embodiment may be, for example, a sheet shape. The thickness of the absorber (for example, the thickness of a sheet-like absorber) may be 0.1 to 20 mm or 0.3 to 15 mm.

[Absorbing Article]

An absorbing article according to the present embodiment includes the absorber according to the present embodiment. Examples of other members constituting the absorbing article include core wraps that retain the shape of the absorber and prevent members constituting the absorber from falling off or flowing; liquid-permeable sheets disposed on the outmost part on the side where a solution to be absorbed enters; and liquid-impermeable sheets disposed on the outmost part on the side opposite to the side where a solution to be absorbed enters. Examples of absorbing articles include diapers (for example, paper diaper), potty training pants, incontinence pads, sanitary material (sanitary napkins, tampons, etc.); sweat pads, pet sheets, members for simple toilets, and materials for treating animal excrement.

FIG. 1 is a cross-sectional view showing an example of an absorbing article. An absorbing article 100 shown in FIG. 1 includes an absorber 10, core wrap sheets 20a and 20b, a liquid-permeable sheet 30, and a liquid-impermeable sheet 40. In the absorbing article 100, the liquid-impermeable sheet 40, the core wrap sheet 20b, the absorber 10, the core wrap sheet 20a, and the liquid-permeable sheet 30 are laminated in that order. In FIG. 1, there is a part in which a gap is shown between members, but the members may be in close contact with each other without the gap.

The absorber 10 includes water-absorbing resin particles 10a and a fiber layer 10b containing a fibrous material. The water-absorbing resin particles 10a are dispersed in the fiber layer 10b. The water-absorbing resin particles 10a are a mixture of the water-absorbing resin particles (A) and the water-absorbing resin particles (B).

The core wrap sheet 20a in contact with the absorber 10 is disposed on one surface side of the absorber 10 (in FIG. 1, the upper side of the absorber 10). The core wrap sheet 20b in contact with the absorber 10 is disposed on the other surface side of the absorber 10 (in FIG. 1, the lower side of the absorber 10). The absorber 10 is disposed between the core wrap sheet 20a and the core wrap sheet 20b. Examples of the core wrap sheets 20a and 20b include tissues, non-woven fabrics, woven fabrics, synthetic resin films having a liquid permeable hole, and net sheets having a mesh. The core wrap sheet 20a and the core wrap sheet 20b have, for example, main surfaces having the same size as that of the absorber 10.

The liquid-permeable sheet 30 is disposed on the outmost part on the side where a solution to be absorbed enters. The liquid-permeable sheet 30 in contact with the core wrap sheet 20a is disposed on the core wrap sheet 20a. Examples of the liquid-permeable sheet 30 include non-woven fabrics and porous sheets made of synthetic resins such as polyethylene, polypropylene, polyester, and polyamide.

The liquid-impermeable sheet 40 is disposed on the outmost part on the side opposite to the liquid-permeable sheet 30 in the absorbing article 100. The liquid-impermeable sheet 40 in contact with the core wrap sheet 20b is disposed on the lower side of the core wrap sheet 20b. Examples of the liquid-impermeable sheet 40 include sheets made of synthetic resins such as polyethylene, polypropylene, and polyvinyl chloride and sheets made of a composite material of these synthetic resins and a non-woven fabric.

The liquid-permeable sheet 30 and the liquid-impermeable sheet 40 have, for example, main surfaces wider than the main surface of the absorber 10, and the outer edges of the liquid-permeable sheet 30 and the liquid-impermeable sheet 40 extend around the absorber 10 and the core wrap sheets 20a and 20b.

The size relationship of the absorber 10, the core wrap sheets 20a and 20b, the liquid-permeable sheet 30, and the liquid-impermeable sheet 40 is not particularly limited, and is appropriately adjusted according to applications of the absorbing article and the like. In addition, the method of retaining the shape of the absorber 10 using the core wrap sheets 20a and 20b is not particularly limited, and as shown in FIG. 1, the absorber may be wrapped with a plurality of core wrap sheets or the absorber may be wrapped with one core wrap sheet.

The lower limit of the diffusion length of the absorbing article using the absorber according to the present embodiment may be 25 cm or more, 28 cm or more, or 30 cm or more, and the upper limit of the diffusion length may be 40 cm or less or 35 cm or less. The upper limit of the re-wet amount of the absorbing articles may be 4.0 g or less, 3.0 g or less, 2.0 g or less, or 1.0 g or less, and the lower limit of the re-wet amount may be 0.01 g or 0.05 g. The upper limit of the absorption rate of the absorbing articles may be 65 seconds or less, 60 seconds or less, 55 seconds or less, or 50 seconds or less, and the lower limit of the absorption rate may be 1 second or more, 5 seconds or more, or 10 seconds or more. The lower limit of the diffusion area of the absorbing articles may be 300 cm$^2$ or more, 315 cm$^2$ or more, 350 cm$^2$ or more, or 400 cm$^2$ or more, and the upper limit of the diffusion area may be 480 cm$^2$ or less or 450 cm$^2$ or less. Each performance of the above absorbing articles is measured by a method described in examples to be described below.

EXAMPLES

Hereinafter, the present invention will be described in more detail with reference to examples. However, the present invention is not limited to these examples.
[Production of Water-Absorbing Resin Particles]

Production Example 1

A round bottom cylindrical separable flask including a reflux condenser, a dropping funnel, a nitrogen gas inlet pipe, and a stirrer and having an inner diameter of 11 cm and an internal volume of 2 L was prepared. A stirrer having stirring blades having two stages of four inclined paddle blades having a blade diameter of 5 cm was used. 293 g of n-heptane and 0.736 g of a maleic anhydride-modified ethylene/propylene copolymer (Mitsui Chemicals, Inc., HI-WAX 1105A) as a dispersing agent were put into the flask and mixed. The mixture in the flask was heated to 80° C. while stirring at 300 rpm, the dispersing agent was dissolved in n-heptane, and the formed solution was then cooled to 50° C.

92.0 g (acrylic acid: 1.03 mol) of an 80.5 mass % aqueous acrylic acid solution as a water-soluble ethylenically unsaturated monomer was put into a beaker having an internal volume of 300 mL, and while cooling from the outside, 147.7 g of a 20.9 mass % aqueous sodium hydroxide solution was added dropwise into the beaker to neutralize 75 mol % of acrylic acid. Next, 0.092 g of hydroxyl ethyl cellulose (Sumitomo Seika Chemicals Co., Ltd., HEC AW-15F) as a thickener, 0.0736 g (0.272 mmol) of potassium persulfate as a radical polymerization initiator, and 0.010 g (0.057 mmol) of ethylene glycol diglycidyl ether as an internal crosslinking agent were added and dissolved to prepare a first-stage aqueous solution.

The first-stage aqueous solution was put into the above separable flask and then stirred for 10 minutes. Then, a surfactant solution in which 0.736 g of a sucrose stearic acid ester (Mitsubishi-Chemical Foods Corporation, Ryoto Sugar Ester S-370, HLB: 3) as a surfactant was dissolved in 6.62 g of n-heptane was put into the flask to obtain a reaction solution. The inside of the system was sufficiently replaced with nitrogen while stirring the reaction solution at a rotational speed of 550 rpm of the stirrer. Then, the flask was immersed in a water bath at 70° C., the reaction solution was heated, and the polymerization reaction was caused to proceed for 60 minutes to obtain a first-stage polymerization slurry solution.

128.8 g (acrylic acid: 1.43 mol) of an 80.5 mass % aqueous acrylic acid solution was put into a beaker having an internal volume of 500 mL, and while cooling from the outside, 159.0 g of a 27 mass % aqueous sodium hydroxide solution was added dropwise to neutralize 75 mol % of acrylic acid. 0.103 g (0.381 mmol) of potassium persulfate as a radical polymerization initiator and 0.0116 g (0.067 mmol) of ethylene glycol diglycidyl ether as an internal crosslinking agent were put into the beaker containing the neutralized aqueous acrylic acid solution and dissolved to prepare a second-stage aqueous solution.

While stirring the stirrer at a rotational speed of 1000 rpm, the first-stage polymerization slurry solution in the flask was cooled to 25° C., and a total amount of the second-stage aqueous solution was added. After the inside of the flask was replaced with nitrogen for 30 minutes, again, the flask was immersed in a water bath at 70° C., the reaction solution was heated, and a second-stage polymerization reaction was performed for 60 minutes to obtain a water-containing gel polymer. Then, the flask was immersed in an oil bath set at 125° C., and 257.7 g of water was extracted to the outside of the system according to azeotropic distillation of n-heptane and water. Then, 4.42 g (0.507 mmol) of a 2 mass % aqueous ethylene glycol diglycidyl ether solution as a surface crosslinking agent was put into the flask, and the mixture was maintained at 83° C. for 2 hours.

In addition, polymer particles (dry product) were obtained by immersing the flask in an oil bath at 125° C. and removing (drying) n-heptane. The polymer particles were passed through a JIS standard sieve having an opening of 850 μm to obtain 228.0 g of the water-absorbing resin particles (B1). The above operation was repeated to produce 2 kg of water-absorbing resin particles (B1) having a median particle size of 352 μm.

Production Example 2

80 g of a mixed solution (1) containing 4 g of polyether polyol (AGC, EXCENOL750ED) and 76 g of distilled water was prepared. 47.6 g of a mixed solution (2) containing 4.76 g of tolylene-2,4-disisocyanate and 42.84 g of acetone was prepared.

Next, the same flask as in Production Example 1 was prepared. 40 g of the water-absorbing resin particles (B1) and 480 g of n-heptane were put into the flask to obtain a dispersion liquid. The mixed solution (1) was added to the dispersion liquid and stirred at room temperature for 30 minutes, the mixed solution (2) was then added and stirred at room temperature for 120 minutes, and a sequential polymerization reaction was caused to proceed on the surface of the water-absorbing resin particles (B1) to obtain a reaction product. Then, the reaction product was heated in an oil bath at 125° C., and while refluxing n-heptane, water and 76 g of acetone were extracted to the outside of the system according to azeotropic distillation of n-heptane and water.

Then, a dry product was obtained by immersing the flask in an oil bath at 125° C. and removing (drying) n-heptane, acetone, and water. The dry product was passed through a JIS standard sieve having an opening of 850 μm to obtain 38.2 g of the water-absorbing resin particles (A1) having a coating layer containing a polyurethane.

Production Example 3

The same flask as in Production Example 1 was prepared. 250 g of n-heptane, 100 g of the water-absorbing resin particles (B1) and 20 g of a maleic anhydride-modified ethylene/propylene copolymer (Mitsui Chemicals, Inc., HI-WAX 1105A) were put into the flask, and stirred at 1000 rpm, heated to 85° C. and stirred for 10 minutes.

Then, a dry product was obtained by performing drying in an oil bath at 125° C. and removing n-heptane. The dry product was passed through a JIS standard sieve having an opening of 850 μm to obtain 111.52 g of water-absorbing resin particles (A2) having a coating layer containing a maleic anhydride-modified ethylene/propylene copolymer.

Production Example 4

100 g of the water-absorbing resin particles (B1) and 5.0 g of hydrophobic silica Nipsil (Tosoh Silica Corporation, product number: SS-30P) were put into a round bottom cylindrical separable flask having a volume of 2 L. Next, while performing dispersing at a rotational speed of 150 rpm using a silicon anchor blade, the flask was immersed in an oil bath at 125° C. and mixing was performed for 20 minutes while maintaining an internal temperature at 100° C.

Then, the oil bath at 125° C. was removed from the round-bottomed flask, and while stirring with a silicon anchor blade, radiative cool was performed until the temperature inside the round-bottomed flask was lowered to room temperature, and thereby a coated resin particle precursor was obtained. The precursor was passed through a JIS standard sieve having an opening of 850 μm to obtain 102.21 g of water-absorbing resin particles (A3) having a coating layer containing hydrophobic silica.

Production Example 5

An absorber mixture composed of water-absorbing resin particles and pulp was removed from diapers for children commercially available in Japan (UNICHARM Corporation, product name: moony air fit, L size, tape type). Next, the pulp was removed from the absorber mixture to obtain about 40 g of water-absorbing resin particles (B2).

Production Example 6

An absorber mixture composed of water-absorbing resin particles and pulp was removed from diapers for children commercially available in Japan (Kao Corporation, product name: Merries bare skin smooth air through (Merries Suhada Sara-sara Airthrough), L size, tape type. Next, the pulp was removed from the absorber mixture to obtain about 42 g of water-absorbing resin particles (B3).

Production Example 7

101.75 g of water-absorbing resin particles (B4) having a coating layer containing amorphous silica were obtained in the same manner as in Production Example 4 except that TOKUSIL (Oriental Silicas Corporation, product number: NP-S) as hydrophilic silica was used in place of hydrophobic silica.

Production Example 8

The same flask as in Production Example 1 was prepared. 293 g of n-heptane and 0.736 g of a maleic anhydride-modified ethylene/propylene copolymer (Mitsui Chemicals, Inc., HI-WAX 1105A) as a dispersing agent were put into the flask and mixed. The mixture in the flask was heated to 80° C. while stirring at 300 rpm, the dispersing agent was dissolved in n-heptane and the formed solution was then cooled to 50° C.

92.0 g (acrylic acid: 1.03 mol) of an 80.5 mass % aqueous acrylic acid solution as a water-soluble ethylenically unsaturated monomer was put into a beaker having an internal volume of 300 mL, and while cooling from the outside, 147.7 g of a 20.9 mass % aqueous sodium hydroxide solution was added dropwise into the beaker to neutralize 75 mol % of acrylic acid. Next, 1.376 g of hydroxyl ethyl cellulose (Sumitomo Seika Chemicals Co., Ltd., HEC AW-15F) as a thickener, 0.0184 g (0.068 mmol) of potassium persulfate as a radical polymerization initiator, 0.0920 g (0.339 mmol) of 2,2'-azobis(2-methylpropionamidine) dihydrochloride as a water-soluble azo polymerization initiator, and 0.0101 g (0.057 mmol) of ethylene glycol diglycidyl ether as an internal crosslinking agent were added and dissolved to prepare a first-stage aqueous solution.

The first-stage aqueous solution was put into the above separable flask and then stirred for 10 minutes. Then, a surfactant solution in which 0.736 g of sucrose stearic acid ester (Mitsubishi-Chemical Foods Corporation, Ryoto Sugar Ester S-370, HLB: 3) as a surfactant was dissolved in 6.62 g of n-heptane was put into the flask to obtain a reaction solution. The inside of the system was sufficiently replaced with nitrogen while stirring the reaction solution at a rotational speed of 400 rpm of the stirrer. Then, the flask was immersed in a water bath at 66° C., the reaction solution was heated, and the polymerization reaction was caused to proceed for 60 minutes while maintaining the temperature at 56° C., and thereby a first-stage polymerization slurry solution was obtained.

Then, while stirring at a rotational speed of 1000 rpm, the flask was immersed in an oil bath set at 125° C., and 108.12 g of water as extracted to the outside of the system according to azeotropic distillation of n-heptane and water. Then, 4.60 g (0.528 mmol) of a 2 mass % aqueous ethylene glycol diglycidyl ether solution as a surface crosslinking agent was put into the flask, and the mixture was maintained at 83° C. for 2 hours.

In addition, polymer particles (dry product) were obtained by immersing the flask in an oil bath at 125° C. and removing (drying) n-heptane. The polymer particles were passed through a JIS standard sieve having an opening of 850 μm to obtain 99.95 g of water-absorbing resin particles (B5).

[Evaluation of Water-Absorbing Resin Particles]

The water-absorbing resin particles were evaluated as follows. The results are shown in Table 1.

(1) Water Retention Capacity

The water retention capacity (room temperature) of the physiological saline solution containing the water-absorbing resin particles was measured by the following procedure. First, a cotton bag (membrane broad No. 60, width 100 mm×height 200 mm) in which 2.0 g of water-absorbing resin particles were weighed was placed in a beaker having an internal volume of 500 mL. 500 g of a physiological saline solution was poured into the cotton bag containing water-absorbing resin particles at once so as not to form lumps, and the upper part of the cotton bag was then bound with a rubber band and left for 30 minutes and thereby the water-absorbing resin particles were swollen. After 30 minutes, the cotton bag was dehydrated for 1 minute using a dehydrator (Kokusan Co., Ltd., product number: H-122) set such that the centrifugal force was 167 G, and the mass Wa [g] of the cotton bag containing the swollen gel after dehydration was measured. The same operation was performed without adding water-absorbing resin particles, the empty mass Wb [g] of the wet cotton bag was measured, and the water retention capacity of the physiological saline solution of the water-absorbing resin particles was calculated from the following formula.

$$\text{Water retention capacity [g/g]} = (Wa - Wb)/2.0$$

(2) Water Absorption Rate According to a Vortex Method 50.0 g of a physiological saline solution was put into a 100 mL beaker with a rotator (8 mm×30 mm, without a ring) and maintained in a thermostatic chamber at 25° C. Then, 2.0 g of water-absorbing resin particles for evaluation were put into the vortex of the physiological saline solution stirred at 600 rpm, and at the same time, measurement was started with a stopwatch. The time when the vortex disappeared and the solution surface became horizontal was set as the end point, and the time (seconds) until the end point was defined as the water absorption rate.

(3) Non-Pressure DW

Figure 2:
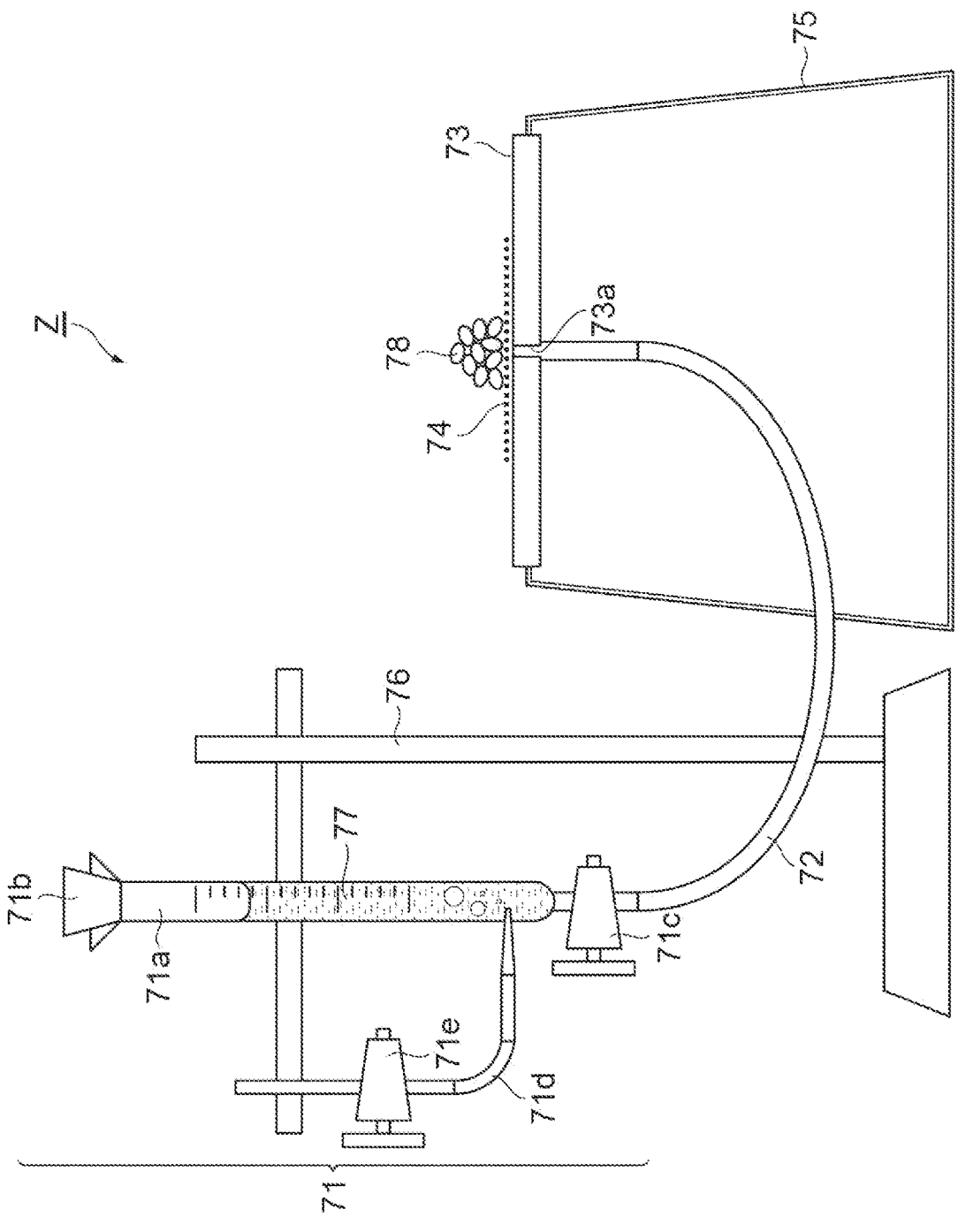
FIG. 2 is a schematic view showing a device for measuring a non-pressure DW of water-absorbing resin particles.

The non-pressure DW of the water-absorbing resin particles was measured using a measurement device Z shown in FIG. 2. The measurement device Z includes a burette part 71, a pipe line 72, a flat measuring table 73, a nylon mesh 74, a pedestal 75, and a clamp 76. The burette part 71 includes a burette 71a with scales, a rubber stopper 71b for sealing the opening of the upper part of the burette 71a, a cock 71c connected to the lower tip of the burette 71a, an air inlet pipe 71d connected to the lower part of the burette 71a and a cock 71e. The burette part 71 was fixed with the clamp 76. The measuring table 73 had a through-hole 73a having a diameter of 2 mm formed in its central part, and was supported by the pedestal 75 of which the height was variable. The through-hole 73a of the measuring table 73 and the cock 71c of the burette part 71 were connected by the pipe line 72. The inner diameter of the pipe line 72 was 6 mm.

The measurement was performed in an environment at a temperature of 25° C. and a humidity of 50±10%. First, the cock 71c and the cock 71e of the burette part 71 were closed, and a physiological saline solution 77 adjusted to 25° C. was put into the burette 71a through the opening of the upper part of the burette 71a. After the opening of the burette 71a was sealed with the rubber stopper 71b, the cock 71c and the cock 71e were opened. The inside of the pipe line 72 was filled with the physiological saline solution 77 so that bubbles did not enter. The height of the measuring table 73 was adjusted so that the height of the water surface of the physiological saline solution 77 that has reached the inside of the through-hole 73a was the same as the height of the upper surface of the measuring table 73. After the adjustment, the height of the water surface of the physiological saline solution 77 in the burette 71a was read on the scale of the burette 71a, and the position was used as a zero point (read value at 0 seconds).

The nylon mesh 74 (40 mm×40 mm, 250 mesh, thickness: about 50 μm) was placed in the vicinity of the through-hole 73a on the measuring table 73, and a cylinder having an inner diameter of 30 mm and a height of 20 mm was placed in its central part. After 1.00 g of water-absorbing resin particles 78 were uniformly sprayed on the cylinder, the cylinder was carefully removed to obtain a sample in which the water-absorbing resin particles 78 were circularly dispersed in the central part of the nylon mesh 74. The nylon mesh 74 on which the water-absorbing resin particles 78 were placed was moved quickly enough to prevent the water-absorbing resin particles 78 from scattering so that the center thereof was the position of the through-hole 73a, and the measurement was started. The time when bubbles were first introduced into the burette 71a from the air inlet pipe 71d was defined as the water absorption start (0 seconds).

The amount of the physiological saline solution 77 decreased in the burette 71a (that is, the amount of the physiological saline solution 77 absorbed by water-absorbing resin particles 78) was sequentially read in units of 0.1 mL, and a decreased amount Wc [g] of the physiological saline solution 77 after 5 minutes were counted from the start of water absorption of the water-absorbing resin particles 78 was read. From Wc, the non-pressure DW 5-minute value was obtained by the following formula. The non-pressure DW was a water absorption amount per 1.00 g of the water-absorbing resin particles 78.

$$\text{Non-pressure } DW \text{ value [mL/g]} = Wc/1.00$$

TABLE 1

| Production Example | Water-absorbing resin particles | Water retention capacity [g/g] | Water absorption rate [seconds] | Non-pressure DW [mL/g] |
|---|---|---|---|---|
| 1 | B1 | 43 | 40 | 54 |
| 2 | A1 | 22 | 67 | 2 |
| 3 | A2 | 35 | 61 | 33 |
| 4 | A3 | 38 | 82 | 15 |
| 5 | B2 | 36 | 25 | 46 |
| 6 | B3 | 37 | 53 | 38 |
| 7 | B4 | 37 | 34 | 60 |
| 8 | B5 | 42 | 153 | 9 |

[Production of Absorber]

Using an airflow mixing device (O-Tec Group, Pad-former), water-absorbing resin particles in the blending amount (g) shown in Table 2 or Table 3 and 8.0 g of crushed pulp (Rayonier Inc, Rayflock) were uniformly mixed by air papermaking, and an absorber core having a size of 40 cm×12 cm was produced. Next, the absorber was placed on tissue paper having a size of 42 cm×14 cm and a basis weight of 16 g/m², 0.6 g was sprayed using a spray containing deionized water, and tissue paper having the same size as the absorber and having a basis weight of 16 g/m² was placed on the absorber to produce a laminate. In addition, a wire mesh having an opening of 2 mm and a size of 42 cm×22 cm was placed on the laminate, a press machine (Imoto Machinery Co., Ltd., small air press machine) was used to press the entire sample by applying a load of 141 kPa for 30 seconds, and thereby an absorber having a water-absorbing resin particle content of 60 mass % was produced.

[Absorbing Article]

A polyethylene air-through type porous liquid-permeable sheet having the same size as the absorber and a basis weight of 22 g/m² was disposed on the upper surface of the absorber, a polyethylene liquid-impermeable sheet having the same size and same basis weight was disposed on the lower surface of the absorber, and the absorber was interposed between the sheets to produce an absorbing article. The following evaluation was performed using the absorbing article.

(Preparation of Test Solution)

9866.0 g of distilled water, 100.0 g of sodium chloride, 3.0 g of calcium chloride dihydrate, 6.0 g of magnesium chloride hexahydrate, 25.0 g of a 1 mass % Triton X solution (a mixture of Triton X-100 manufactured by FUJIFILM Wako Pure Chemical Corporation and water), and 0.25 g of Food Blue No. 1 (for coloring) were mixed to prepare a test solution.

(Absorption Rate)

The test was performed in a room adjusted to 25° C. and a humidity of 50% (RH). The absorbing article was placed on a horizontal table, and a solution-filling cylinder (with a weight of 60 g) having an opening with an inner diameter of 3 cm was placed in the central part of the absorbing article. Next, 150 mL of a test solution was quickly put into the cylinder. The time from when addition of the test solution started until the test solution was completely absorbed by the absorbing article was measured, and defined as a absorption rate (seconds).

(Re-Wet Amount)

The cylinder was removed, and after 5 minutes were counted from when the test solution was added, about 75 g of filter paper (ADVANTEC No. 51A, formed to 100 mm×100 mm) whose mass was measured in advance was placed near the center of the absorbing article, a weight of about 0.7 psi (with a bottom of 100 mm×100 mm, 5.0 kg) was quickly placed thereon, and a load was applied for 5 minutes. Then, the weight and the filter paper were removed, and the mass of the test solution absorbed by the filter paper was measured. The amount of increase in the mass of the filter paper before and after the test was defined as a re-wet amount (g).

(Diffusibility)

After 10 minutes from when the test solution was added, the distance of the solution spread in the absorbing article was measured using a plastic ruler having a length of 50 cm, and the distance was defined as a diffusion length (cm). The diffusion length was measured when the polyethylene air-through type porous liquid-permeable sheet was removed from the absorbing article so that the diffused test solution was clearly visible and the absorber was exposed. In addition, the diffusion length was a partial length of the stain formed on the surface of the absorber, specifically, a length of a part of the stain formed on the surface of the absorber that passed through the test solution input part (a part corresponding to the central part of the cylinder when the test solution was added) and extended parallel to the long side of the absorber.

Next, using a unipack (Seisannipponsha Ltd., product number: L-4 polyethylene material, size: 480 min×340 mm, thickness: 0.04 mm), the unipack was cut along the outline of the stain formed on the surface of the absorber to produce a film A (Fa), and the mass was measured. In addition, using the same unipack, 10 sheets of the film B cut into a length of 100 mm×a width of 100 mm (an area of 10000 mm²) were produced, and the mass was measured to obtain an average mass (Fb) per film B. The diffusion area (cm²) in the absorbing article was calculated by the following formula.

$$\text{Diffusion area (cm}^2) = \{(Fa/Fb) \times \text{area of } Fb \text{ (10000 mm}^2)\}/100$$

TABLE 2

| | | Example | | | | | | | |
|---|---|---|---|---|---|---|---|---|---|
| | | 1 | 2 | 3 | 4 | 5 | 6 | 7 | 8 |
| Water-absorbing resin particles (A) | A1 | 2 | 4 | 8 | 10 | 8 | 8 | — | — |
| | A2 | — | — | — | — | — | — | 8 | — |
| | A3 | — | — | — | — | — | — | — | 8 |

TABLE 2-continued

| | | Example | | | | | | | |
|---|---|---|---|---|---|---|---|---|---|
| | | 1 | 2 | 3 | 4 | 5 | 6 | 7 | 8 |
| Water-absorbing | B1 | 10 | 8 | 4 | 2 | — | — | 4 | 4 |
| resin particles (B) | B2 | — | — | — | — | 4 | — | — | — |
| | B3 | — | — | — | — | — | 4 | — | — |
| Absorption rate [seconds] | | 60 | 59 | 51 | 49 | 61 | 59 | 56 | 60 |
| Re-wet amount (g) | | 3.0 | 0.7 | 0.6 | 0.7 | 0.3 | 0.3 | 0.4 | 0.5 |
| Diffusion distance (cm) | | 25 | 26 | 30 | 28 | 33 | 34 | 26 | 26 |
| Diffusion area (cm²) | | 311 | 316 | 366 | 343 | 406 | 423 | 323 | 333 |

TABLE 3

| | | Comparative Example | | | | | | | | |
|---|---|---|---|---|---|---|---|---|---|---|
| | | 1 | 2 | 3 | 4 | 5 | 6 | 7 | 8 | 9 |
| Water-absorbing resin particles (A) | A1 | — | 1 | 11 | — | — | — | — | — | — |
| Water-absorbing resin particles (B) | B1 | 12 | 11 | 1 | 10 | 8 | 4 | 10 | 8 | 4 |
| | B4 | — | — | — | 2 | 4 | 8 | — | — | — |
| | B5 | — | — | — | — | — | — | 2 | 4 | 8 |
| Absorption rate [seconds] | | 64 | 63 | 69 | 57 | 56 | 60 | 76 | 79 | 88 |
| Re-wet amount (g) | | 2.9 | 3.1 | 0.4 | 0.8 | 0.6 | 0.4 | 7.0 | 1.5 | 1.6 |
| Diffusion distance (cm) | | 24 | 25 | 33 | 24 | 24 | 24 | 25 | 30 | 32 |
| Diffusion area (cm²) | | 304 | 311 | 416 | 301 | 296 | 291 | 313 | 376 | 396 |

REFERENCE SIGNS LIST

10: absorber, 10a, 78: water-absorbing resin particles, 10b: fiber layer, 20a, 20b: core wrap sheet, 30: liquid-permeable sheet, 40: liquid-impermeable sheet, 71: burette part, 71a burette, 71b: rubber stopper, 71c, 71e: cock, 71d: air inlet pipe, 72: pipe line, 73: measuring table, 74: nylon mesh, 73a: through-hole, 75: pedestal, 76: clamp, 77: physiological saline solution, 100: absorbing article, z: measurement device.

The invention claimed is:

1. An absorber comprising water-absorbing resin particles, wherein the water-absorbing resin particles comprise water-absorbing resin particles (A) that have a water absorption rate of 61 to 150 seconds according to a Vortex method and have a non-pressure DW 5-minute value of 36 mL/g or less, wherein the content of the water-absorbing resin particles (A) based on a total amount of the water-absorbing resin particles is 20 to 90 mass %, wherein the water-absorbing resin particles comprise water-absorbing resin particles (B) different from the water-absorbing resin particles (A), and wherein the water-absorbing resin particles (B) have a water absorption rate of less than 55 seconds according to a Vortex method and a non-pressure DW 5-minute value of more than 36 mL/g.

2. The absorber according to claim 1, wherein the water-absorbing resin particles (A) are coated resin particles having a water-insoluble coating layer that covers at least a part of the surface of the water-absorbing resin particles.

3. The absorber according to claim 2, wherein the coating layer is a layer comprising at least one water-insoluble component selected from among water-insoluble organic compounds and water-insoluble inorganic compounds.

4. The absorber according to claim 3, wherein the water-insoluble organic compounds comprise at least one organic compound selected from the group consisting of polyurethanes, polyolefins, polyesters, polyamides, polystyrenes, polycarbonates, polyacrylates, polyacetals, and acid-modified products thereof.

5. The absorber according to claim 3, wherein the water-insoluble inorganic compounds comprise at least one inorganic compound selected from the group consisting of light anhydrous silicic acid, calcium silicate, silicon dioxide, talc, silicon monoxide, and synthetic hydrotalcite.

6. The absorber according to claim 1, wherein the water-absorbing resin particles (A) have a water absorption rate of 63 to 150 seconds according to a Vortex method and have a non-pressure DW 5-minute value of 36 mL/g or less.

7. The absorber according to claim 1, wherein the water-absorbing resin particles (A) have a water absorption rate of 65 to 150 seconds according to a Vortex method and have a non-pressure DW 5-minute value of 36 mL/g or less.

8. The absorber according to claim 1, wherein the water-absorbing resin particles (A) have a water absorption rate of 61 to 150 seconds according to a Vortex method and have a non-pressure DW 5-minute value of 1 mL/g or more and 36 mL/g or less.

9. The absorber according to claim 1, wherein the water-absorbing resin particles (A) have a water absorption rate of 63 to 150 seconds according to a Vortex method and have a non-pressure DW 5-minute value of 1 mL/g or more and 36 mL/g or less.

10. The absorber according to claim 1, wherein the water-absorbing resin particles (A) have a water absorption rate of 65 to 150 seconds according to a Vortex method and have a non-pressure DW 5-minute value of 1 mL/g or more and 36 mL/g or less.

11. The absorber according to claim 1, wherein the water-absorbing resin particles comprise a crosslinked polymer formed by polymerization of monomers comprising ethylenically unsaturated monomers.

12. The absorber according to claim 11, wherein the ethylenically unsaturated monomers comprise at least one compound selected from the group consisting of (meth) acrylic acid and salts thereof, acrylamide, methacrylamide, and N,N-dimethylacrylamide.

13. The absorber according to claim 11, wherein the ethylenically unsaturated monomers comprise at least one compound selected from the group consisting of (meth) acrylic acid and salts thereof, and acrylamide.

* * * * *